US007648113B2

(12) United States Patent
Johnson (10) Patent No.: US 7,648,113 B2
(45) Date of Patent: Jan. 19, 2010

(54) SUPPORT FOR A CYLINDRICALLY-SHAPED ACCESSORY

(76) Inventor: Ruben Johnson, 3609 W. Castile Ct., Peoria, IL (US) 61615

( * ) Notice: Subject to any disclaimer, the term of this patent is extended or adjusted under 35 U.S.C. 154(b) by 95 days.

(21) Appl. No.: 11/879,572

(22) Filed: Jul. 18, 2007

(65) Prior Publication Data

US 2009/0020667 A1 Jan. 22, 2009

(51) Int. Cl.
*A47K 1/08* (2006.01)
(52) U.S. Cl. ............... 248/311.2; 248/315; 224/148.6; 220/647; 220/649
(58) Field of Classification Search ............. 248/311.2, 248/315, 314, 218.4; 224/148.6, 148.5
See application file for complete search history.

(56) References Cited

U.S. PATENT DOCUMENTS

| D56,662 S | * | 11/1920 | Lauzon | D2/633 |
| 4,176,773 A | * | 12/1979 | Wilkinson | 224/604 |
| 4,790,462 A | * | 12/1988 | Kawaguchi | 224/250 |
| 5,407,110 A | * | 4/1995 | Marsh, Jr. | 224/148.6 |
| 5,622,346 A | * | 4/1997 | Story, Jr. | 248/311.2 |
| 6,390,427 B1 | * | 5/2002 | McConnell et al. | 248/231.61 |
| 7,188,855 B1 | * | 3/2007 | Thomas | 280/304.1 |
| 2002/0179282 A1 | * | 12/2002 | Kutzner | 165/41 |
| 2003/0019992 A1 | * | 1/2003 | Webb | 248/311.2 |

* cited by examiner

Primary Examiner—Amy J Sterling (57) ABSTRACT

A support for a cylindrically-shaped accessory has a first frame defining a receptacle for a cylindrically-shaped accessory and a connecting assembly. The first frame has a bottom wall and a peripheral bracing wall structure. The bottom wall defines an upwardly facing surface. The peripheral bracing wall structure extends at least partially around a region occupied by a cylindrically-shaped accessory in the upright stored orientation, bearing on the upwardly-facing surface, to thereby limit tipping of the cylindrically-shaped accessory. The connecting assembly has first and second connector parts attachable one each to the first frame and second frame upon which the support can be placed. The first and second connector parts are engagable, each with the other, by relatively translating the first and second connector parts along a connecting line.

24 Claims, 7 Drawing Sheets

SUPPORT FOR A CYLINDRICALLY-SHAPED ACCESSORY

BACKGROUND OF THE INVENTION

1. Field of the Invention

This invention relates to a support for a cylindrically-shaped accessory, such as one for a pressurized supply of a gas, that can be attached to a fixed frame or a frame on a movable component, such as a wheelchair, walker, scooter, or the like.

2. Background Art

Persons with respiratory conditions are commonly required to intake oxygen to facilitate breathing. Portable systems are currently available which allow a user to transport the system on his/her person while selectively controlling the amount of oxygen that is delivered.

Many individuals with respiratory conditions are either bound to a wheelchair or periodically use the same while sitting at a particular location or navigating between locations. To accommodate individuals' need for oxygen, oxygen cylinders are typically provided on the wheelchair and situated behind the location at which the user is seated. The conventional wheelchair frame is constructed to conveniently support the oxygen cylinder at that location.

While mounting of the cylinder behind where the user is seated offers a convenience from the standpoint of mounting the support therefor, this location has a drawback in that it does not permit a user to conveniently operate the valves and controls associated with the cylinder while in a seated position or to place the cylinder in, or remove the cylinder from, the receptacle with the user in a seated orientation. A user that is ambulatory may be able to elevate from the seat and move around the wheelchair to effect the desired control of the oxygen delivery and/or reposition the cylinder. However, those with limited, or no, ability to ambulate may be dependent upon others to assist in carrying out these tasks. This represents not only an inconvenience, but a potential danger to the health of the user, particularly if assistance is not always and readily available.

While ideally the oxygen cylinder would be mounted in the front region of the wheelchair to be accessible to a user, the industry has opted to mount oxygen cylinders inconveniently behind the user to take advantage of the supporting structural framework of conventional wheelchairs.

Users of oxygen also contend with the above problems when operating motorized scooters and using ambulatory assist devices, such as a walker. In the latter case, it is common for a user to have a wheeled stand, separate from the walker, that supports the oxygen cylinder. If the individual is unassisted, he/she must not only manipulate the walker, but also move the stand with the oxygen cylinder thereon. This may necessitate that the user stop and move the stand after each step, which is an obvious inconvenience.

Alternatively, one utilizing a walker may require that an individual walk by his/her side and move the stand with the oxygen cylinder thereon in step with the user. This greatly limits the user's independence.

Another problem contended with by users of oxygen is the transportation of the cylinders themselves. Because the cylinders are required to confine a gas under pressure, they are generally made from relatively thick metal material that makes them quite heavy. The control assemblies thereon add additional weight to the cylinders.

Aside from their weight making repositioning inconvenient, gas cylinders generally are not equipped with any structure that facilitates their lifting and transportation. It is common to see a user grasp the cylinder at the control assembly and potentially additionally at the bottom of the cylinder to effect lifting thereof. Thus, it is generally inconvenient and awkward for a person to place an oxygen cylinder at the useable site and/or effect an exchange thereof with a filled cylinder at the appropriate time.

In spite of there being a significant volume of users of oxygen in homes, nursing centers, and hospitals, the industry has contended with the above problems because of the lack of viable solutions therefor. Ideally, designers of health care equipment would develop oxygen cylinder mounting systems that would facilitate stable mounting of the cylinders in a simple yet safe manner, facilitate replacement, handling and transportation, allow user access to the controls therefor, and not require any significant modification to a frame upon which the cylinders and their supports are mounted in homes and public facilities.

SUMMARY OF THE INVENTION

In one form, the invention consists of a support for a cylindrically-shaped accessory. The support has a first frame defining a receptacle for a cylindrically-shaped accessory and a connecting assembly. The first frame in turn has a bottom wall and a peripheral bracing wall structure. The bottom wall defines an upwardly facing surface against which a cylindrically-shaped accessory can be placed in an upright stored orientation wherein a central axis of the cylindrically-shaped accessory in the upright stored orientation extends generally vertically. The peripheral bracing wall structure extends at least partially around a region occupied by a cylindrically-shaped accessory in the upright stored orientation to thereby limit tipping of the cylindrically-shaped accessory from the upright stored orientation. The connecting assembly has first and second connector parts. The first connector part is on the first frame. The second connector part is attachable to a second frame upon which the support can be placed in an operative state. The first and second connector parts are engagable, each with the other, by relatively translating the first and second connector parts along a connecting line between a separated position and an engaged position wherein the support is in the operative state. The first and second connector parts in the engaged position prevent relative movement between the first and second connector parts in directions other than along the connecting line.

In one form, the cylindrically-shaped accessory contains a pressurized supply of a gas and has a control assembly thereon.

In one form, the combination includes a second frame to which the second connector part is attached. The second frame is defined on one of: a) a wheeled device capable of seating and transporting a user; b) a walker; and c) a fixed wall.

In one form, the combination includes a second frame to which the second connector part is attached. The second frame is defined on a wheeled device capable of seating and transporting a user in a seated orientation. The second connector part is situated so that with the support in the operative state, a user in the seated orientation on the wheeled device can access the cylindrically-shaped accessory to at least one of: a) operate the control assembly with the cylindrically-shaped accessory in the upright stored orientation; and b) change the cylindrically-shaped accessory between a separated position and the upright stored orientation.

In one form, the peripheral bracing wall structure has a first ring extending around the receptacle with a first vertically extending axis and a vertically extending first reinforcing strap that maintains the first ring in an elevated position above the upwardly facing surface.

In one form, the peripheral bracing wall structure has a second ring extending around the receptacle with a second vertically extending axis, that is substantially coincident with the first vertically extending axis. The first reinforcing strap connects between the first and second rings.

In one form, the peripheral bracing wall structure has a vertically extending second reinforcing strap that connects between the first and second rings.

In one form, the first and second reinforcing straps are generally diametrically oppositely located with respect to each other.

In one form, the peripheral bracing wall structure has a third ring extending around the receptacle with a vertically extending third axis. The reinforcing strap connects between the first, second and third rings.

In one form, the peripheral bracing wall structure has first and second vertically spaced rings extending around the receptacle and the bottom wall is on one of the first and second rings.

In one form, the one of the first and second rings has a top and bottom and the upwardly facing surface resides between the top and bottom of the one of the first and second rings.

In one form, the one of the first and second rings has a continuous wall that extends around the receptacle and the bottom wall is formed as one piece with the continuous wall.

In one form, the first ring is made from plastic and the first reinforcing strap is made from metal.

In one form, the first ring has a curved surface and the first strap is substantially flat and locally shaped to conform to the curved surface.

A lifting strap may be attached to the first frame to reside between the curved surface and a cylindrically-shaped accessory in the upright stored orientation.

The support may be provided in combination with a cylindrically-shaped accessory in the upright stored orientation. The lifting strap has a downwardly opening U-shaped surface upon which a lifting force can be applied by a user to elevate the support together with the cylindrically-shaped accessory in the upright stored orientation. The lifting strap is configured to wedge between the cylindrically-shaped accessory and curved surface bounding the receptacle so as to urge the cylindrically-shaped accessory against the curved surface bounding the receptacle.

In one form, the lifting strap is defined by a flexible material that becomes wedged between the cylindrically-shaped container and curved surface bounding the receptacle by applying a tensioning force to the lifting strap.

In one form, the receptacle is cylindrically shaped with a vertical central axis and the lifting strap has spaced first and second legs that are attached one each to the first frame at first and second locations spaced circumferentially around the vertical central axis of the receptacle.

In one form, the first and second legs are attached to the first frame for pivoting movement relative to the frame respectively around first and second axes.

In one form, the invention consists of a cylindrically-shaped container and a support for the cylindrically-shaped container. The support has a first frame having a first ring with a first central axis and a second ring with a second central axis. First and second reinforcing straps extend between the first and second rings. The first and second reinforcing straps maintain the first and second rings in coaxial and axially spaced relationship and are circumferentially spaced from each other with respect to the central axes. A bottom wall defines an upwardly facing surface. The first and second rings and upwardly facing surface bound a receptacle into which the cylindrically-shaped container is directed into an upright stored orientation in which the cylindrically-shaped container bears on the upwardly facing surface and is surrounded by the first and second rings. The cylindrically-shaped container is translatable relative to the support selectively: i) axially downwardly from a separated position into the upright stored orientation within the receptacle; and ii) axially upwardly from the upright stored orientation to be separated from the support.

In one form, the first ring has a curved surface and the first reinforcing strap is substantially flat and locally shaped to conform to the curved surface.

In one form, the lifting strap defines an inverted U-shaped surface upon which a lifting force can be applied. The lifting strap is configured so that application of a tensioning force on the lifting strap causes the lifting strap to wedge the cylindrically-shaped accessory against the first frame.

DETAILED DESCRIPTION OF THE DRAWINGS

Figures 1, 2, 5, 6:
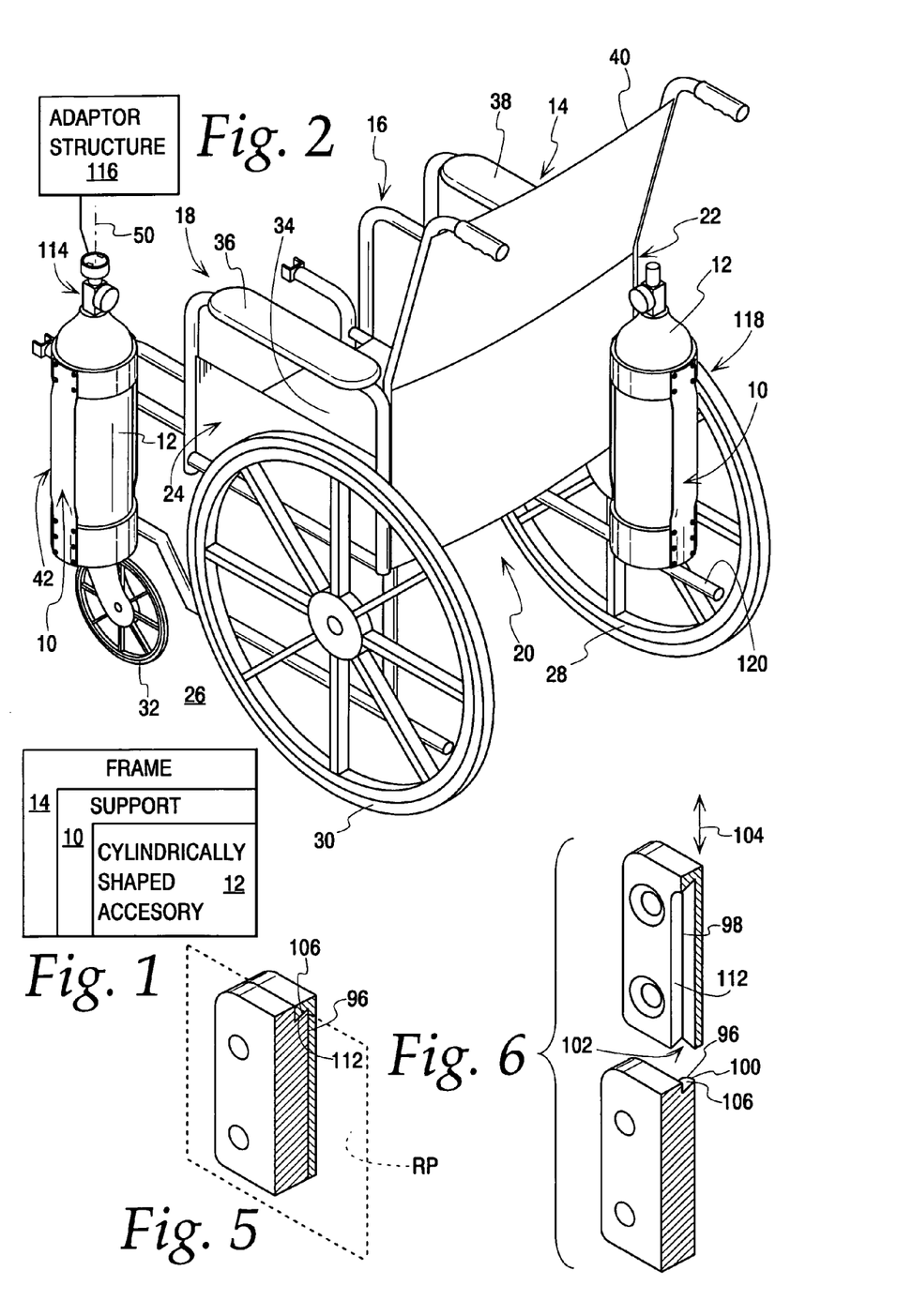
FIG. 1 is a schematic representation of the combination of a frame and a support for a cylindrically-shaped accessory, according to the present invention.
FIG. 2 is a perspective view of a wheelchair, support, and cylindrically-shaped accessory, as shown schematically in FIG. 1, and with the cylindrically-shaped accessory in an upright, stored orientation within the support and shown at a preferred, front location and at an optional, rear location.
FIG. 5 is an enlarged, cross-sectional view of cooperating connector parts mounted one each to the support and wheelchair frame.
FIG. 6 is an enlarged view as in FIG. 5 wherein the connector parts are separated.

As seen in FIG. 1, the present invention is directed to a support 10 for a cylindrically-shaped accessory 12 that is mounted upon a suitable frame 14. The structure in FIG. 1 is shown schematically in that the invention contemplates virtually an unlimited number of variations from the particular structure described below with respect to FIGS. 2-6. It is intended that the support 10 can define a receptacle for any type of cylindrically-shaped accessory 12. Further, the frame 14 can take virtually an unlimited number of forms, only some of which are described below.

As seen in FIGS. 2-6, the frame 14 is part of a wheelchair 16 having a front 18, back 20, and laterally spaced sides 22, 24. The wheelchair 16 is supported upon a subjacent surface 26 for rolling movement thereagainst by a plurality of wheels, and more particularly, laterally spaced rear wheels 28, 30, and front wheels 32 (one shown). It is conceivable that a single front wheel might be utilized.

A seating surface 34 is provided on the frame 16 upon which a user can be supported in a seated orientation. In the seated orientation, the user can rest his/her arms upon side rests 36, 38. In the seated orientation, the user's back can be supported upon a vertically extending surface 40.

Figure 3:
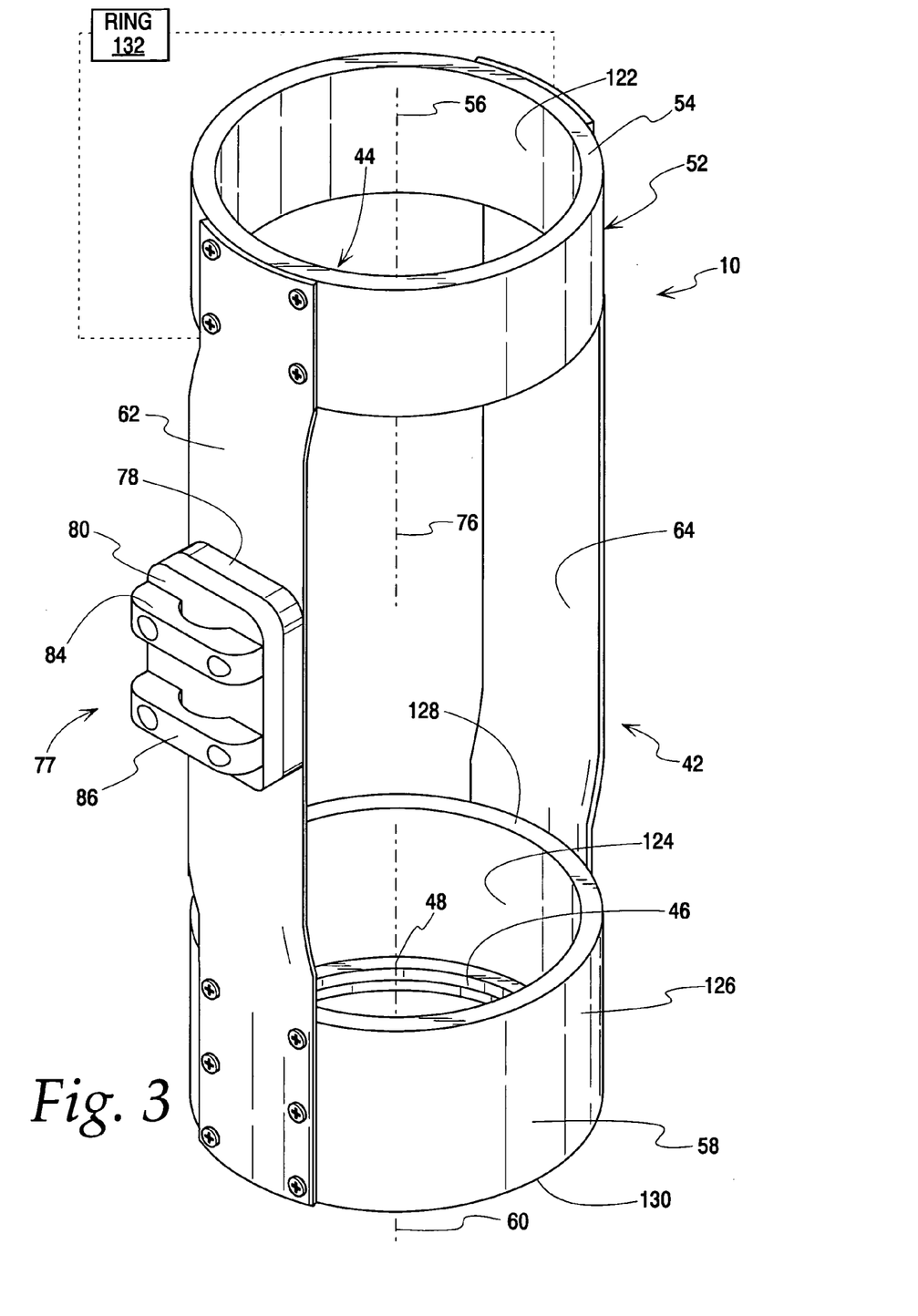
FIG. 3 is an enlarged, perspective view of the support shown in FIG. 2.
Figures 4, 7:
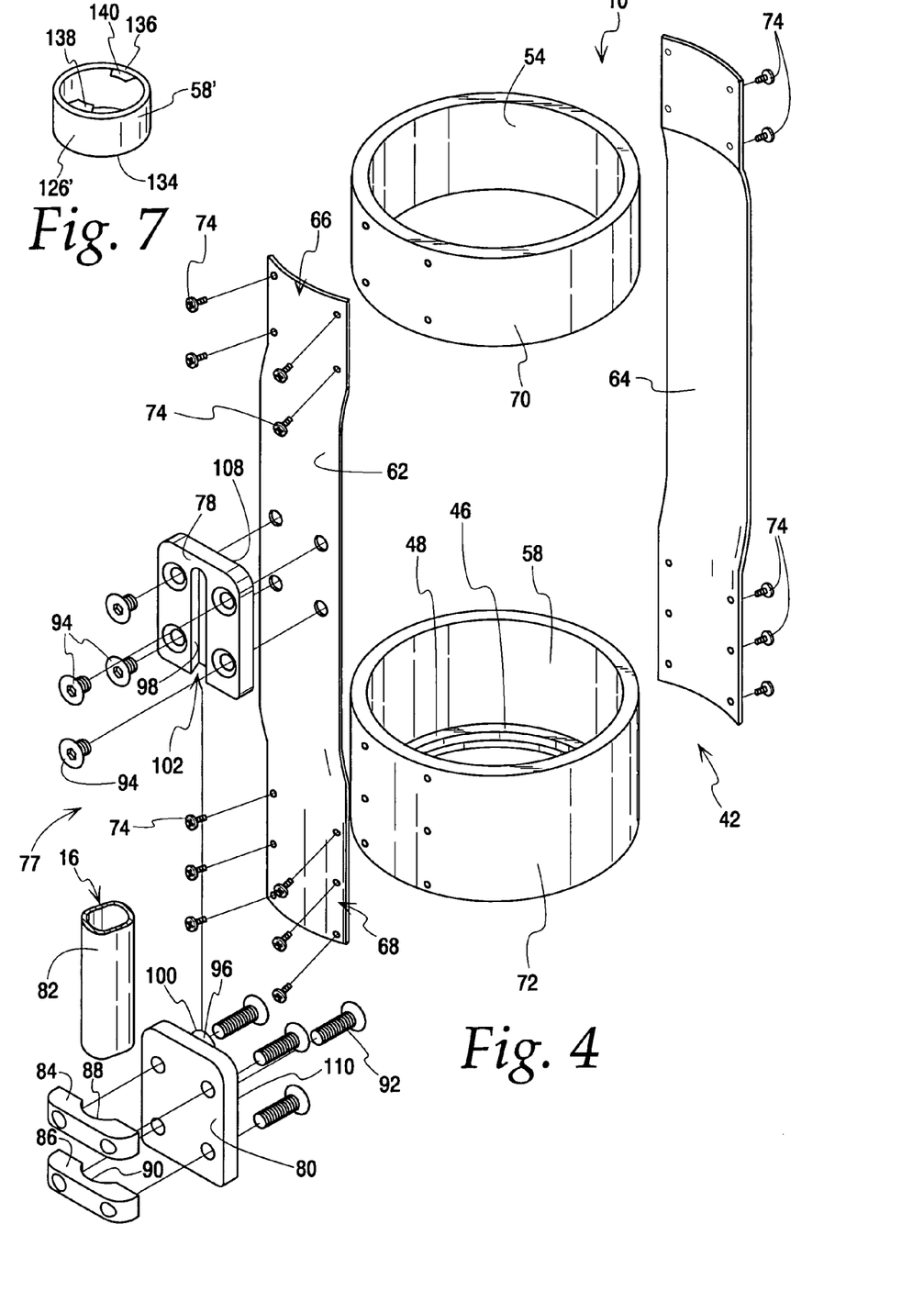
FIG. 4 is an enlarged, exploded, perspective view of the support in FIGS. 2 and 3.
FIG. 7 is a reduced, inverted, perspective view of part of a modified form of support, according to the invention.

The support 10 consists of a frame 42 defining a cylindrically-shaped receptacle 44 for the cylindrically-shaped accessory 12, which is shown as a cylinder/cylindrical container for a pressurized supply of gas, such as oxygen.

The frame 42 consists of a bottom wall 46 defining an upwardly facing surface 48 against which the cylindrical container 12 can be placed in an upright, stored orientation, as shown in FIG. 2. The cylindrical container 12 has a central axis 50 that extends substantially vertically with the cylindrical container 12 in the upright stored orientation.

The frame 42 further includes a peripheral bracing wall structure 52 extending at least partially around the region within the receptacle 44 occupied by the cylindrical container 12 in its upright stored orientation, thereby to limit tipping of the cylindrical container 12.

The peripheral bracing wall structure 52 consists of at least one upper ring 54 with a vertically extending central axis. In this embodiment, the bottom wall 46 is defined on a lower ring 58 having a central axis 60. The upper and lower rings 54, 58 are concentric and axially spaced from each other.

With the cylindrical container 12 in the upright stored orientation, the cylindrical container 12 bears upon the upwardly facing surface 48 and is surrounded by both the upper and lower rings 54, 58 that extend around and bound the receptacle 44.

The peripheral bracing wall structure 52 further includes at least one, and in a preferred form two, vertically extending, reinforcing straps 62, 64. In this embodiment, the reinforcing straps 62, 64 are circumferentially spaced to be diametrically opposite with respect to the concentric axes 56, 60 of the rings 54, 58, respectively.

In this embodiment, the reinforcing straps 62, 64 are each made from flat stock. The strap 62 is locally shaped at its top 66 and bottom 68 to be curved to conform to curved outer surfaces 70, 72, respectively on the upper and lower rings 54, 58. Threaded fasteners 74 are directed through the strap 62 at the top 66 and bottom 68 thereof to rigidly secure the strap 62 to the rings 54, 58.

The strap 64 may be identical to the strap 62 and is connected at a diametrically opposite location to the rings 54, 58 in like fashion, using the same type of fasteners 74.

With the support 10 in an upright, operative state, the receptacle 44 is configured to allow the cylindrical container 12 to be translated along the vertically extending axis 76 of the receptacle 44 relative to the support 10 selectively: a) vertically downward from a separated position into the upright stored orientation; and b) upwardly from the upright stored orientation to be separated from the support 10.

To secure the support 10 to the wheelchair 16, a connecting assembly 77 is utilized consisting of cooperating connector parts 78, 80, provided one each on the support 10 and wheelchair frame 14. The connector part 80 is designed to be secured to a vertically extending tubular component 82 on the wheelchair frame 14. To accomplish this, saddle-shaped clamp elements 84, 86 are utilized. The clamp elements 84, 86 have surfaces 88, 90 that nominally conform to the shape of the tubular component 82. Threaded fasteners 92 are directed through the connector part 80 and into the clamp element 84, 86 so that the tubular component 82 is captively and fixedly held therebetween. This described arrangement allows the connector part 80 to be located, and fixedly maintained, at any desired location and height.

The connector part 78 is secured to the reinforcing strap 62 through threaded fasteners 94. The connector part 80 has a vertically extending rib 96 that can be directed into a complementary receptacle 98 on the connector part 78. This is accomplished by aligning the top 100 of the rib 96 at a bottom entry location 102 for the receptacle 98 and relatively translating the connector parts 78, 80 along a vertical connecting line, indicated by the double-headed arrow 104. The connector parts 78, 80 are pre-attached to their respective frames 42, 16 preparatory to their engagement. The frame 42 on the support 10 is translated downwardly relative to the wheelchair frame 14 to effect engagement of the connector parts 78, 80. Once engaged, the connector parts 78, 80 are rigidly and stably held together and precluded from being moved relative to each other, other than along the connecting line 104.

The surface 106 extending around the rib 96 is non-perpendicular to a reference plane RP defined parallel to facing, flat surfaces 108, 110 on the connector parts 78, 80, which surfaces potentially slide one against the other as the rib 96 moves fully into the receptacle 98 during the engagement process. The receptacle 98 is bounded by a complementary surface 112. As a result of the relationship between the surfaces 106, 112, the connector parts 78, 80 are precluded from being separated through forces applied on the connector parts 78, 80 oppositely and orthogonally to the reference plane RP. Suitable connectors are also shown in my corresponding U.S. Pat. No. 5,687,942, which is incorporated herein by referenced.

As shown in FIG. 2, a preferred location for mounting the cylindrical container 12 is at one of the sides 24 of the frame 14, forwardly of the axis of the rear wheel 30, and more preferably fully forwardly of the wheel 30. In this configuration, the cylindrical container 12 also resides forwardly of the side rest 36 whereby a user in the seated orientation can easily access the cylindrical container 12 as to operate a conventional-type control assembly 114 at the top thereof, and facilitates connection of adaptor structure 116 through which the user can establish an oxygen flow path between the cylindrical container 12 and the user. For example, the adaptor structure 116 may include tubing and connectors at the control assembly 114, and additional fittings for facilitating delivery of the oxygen at the front of the user's face. The control assembly 114 may include valves, etc. typically provided on the cylindrical container 12 that allow initial delivery, volume control, and monitoring of the delivered oxygen.

It is also contemplated that the support 10 may be mounted so that the user by himself/herself may remove a cylindrical container 12 and replace the same with a filled container 12 from the seated orientation.

This location is preferred over a conventional location for cylinders, shown at 118 behind where the user is seated. The inventive support 10 with the cylindrical container 12 in an upright stored orientation is shown at this location, which is made possible using the same connecting structure. Typically, prior art containers, using conventional supports, are mounted at this location to utilize the cantilevered frame component 120 that defines a convenient support for objects to be attached to the wheelchair 16. As noted above, it is preferred that the user in the seated orientation be able to access the cylindrical container 12 that is at a location that is not fully behind where the user resides in the seated orientation.

The support 10 lends itself to construction in a number of different manners and from many different materials. In one exemplary form, the reinforcing straps 62, 64 are made from a light metal material, such as aluminum. The rings 54, 58 may be made from plastic with inside curved surfaces 122, 124 that smoothly guide the cylindrical container 12 or other cylindrically-shaped accessory into and from the receptacle 44.

In the embodiment shown, the lower ring 58 consists of a continuous wall 126 that extends around the axis 48. The bottom wall 46 and continuous wall 126 in this embodiment are formed as one piece. The bottom wall 46 in this embodiment resides between the top 128 and bottom 130 of the ring 58.

In one variation, an additional, optional ring 132, as shown in FIG. 3, can be incorporated using the reinforcing straps 62, 64, thereby to increase the vertical extent of the receptacle 44. Different numbers of rings are contemplated, from as few as one, to potentially more than three. In each embodiment, preferably the rings 54, 58, 132 surround at least a part of the cylindrical container 12, and more preferably fully surround the same.

A modified form of the lower ring 58 is shown at 58' in FIG. 7. In this embodiment, rather than forming the continuous wall 126 and bottom wall 46 as one piece, the continuous wall 126' is shown with a consistent inside and outside diameter between the top 134 and bottom 136 thereof. At the bottom 136, one or more bottom wall pieces 138, 140 are provided and secured thereto as by use of an adhesive, welding, brazing, separate fasteners, etc.

With the inventive structure, the support 10 an be conveniently mounted to the wheelchair 16 at any of a number of desired locations and with an adjustable height. With the connector part 80 installed at a desired location, the support 10 and the attached connector part 78 can be conveniently installed upon and separated from the wheelchair frame 14 with the cooperating connecting part 80 thereon. With the support 10 in the preferred operative position, the user can conveniently install and replace the cylindrical container 12 as well as operate the control assembly 114 thereon, potentially without any outside assistance. This offers the user a convenience as well as assuring that the user can safely control the delivery of oxygen that may be needed.

Many variations from the basic structure described above are contemplated. The manner of connecting the support 10 to the wheelchair frame 14, described above, is exemplary in nature only. Any manner of connection, other than that disclosed, is contemplated.

The materials of construction, while described specifically above, are not limited. The support 10 can be made from any material or combination of materials, among which are plastic, metal, composite, etc.

Figures 8, 9, 10:
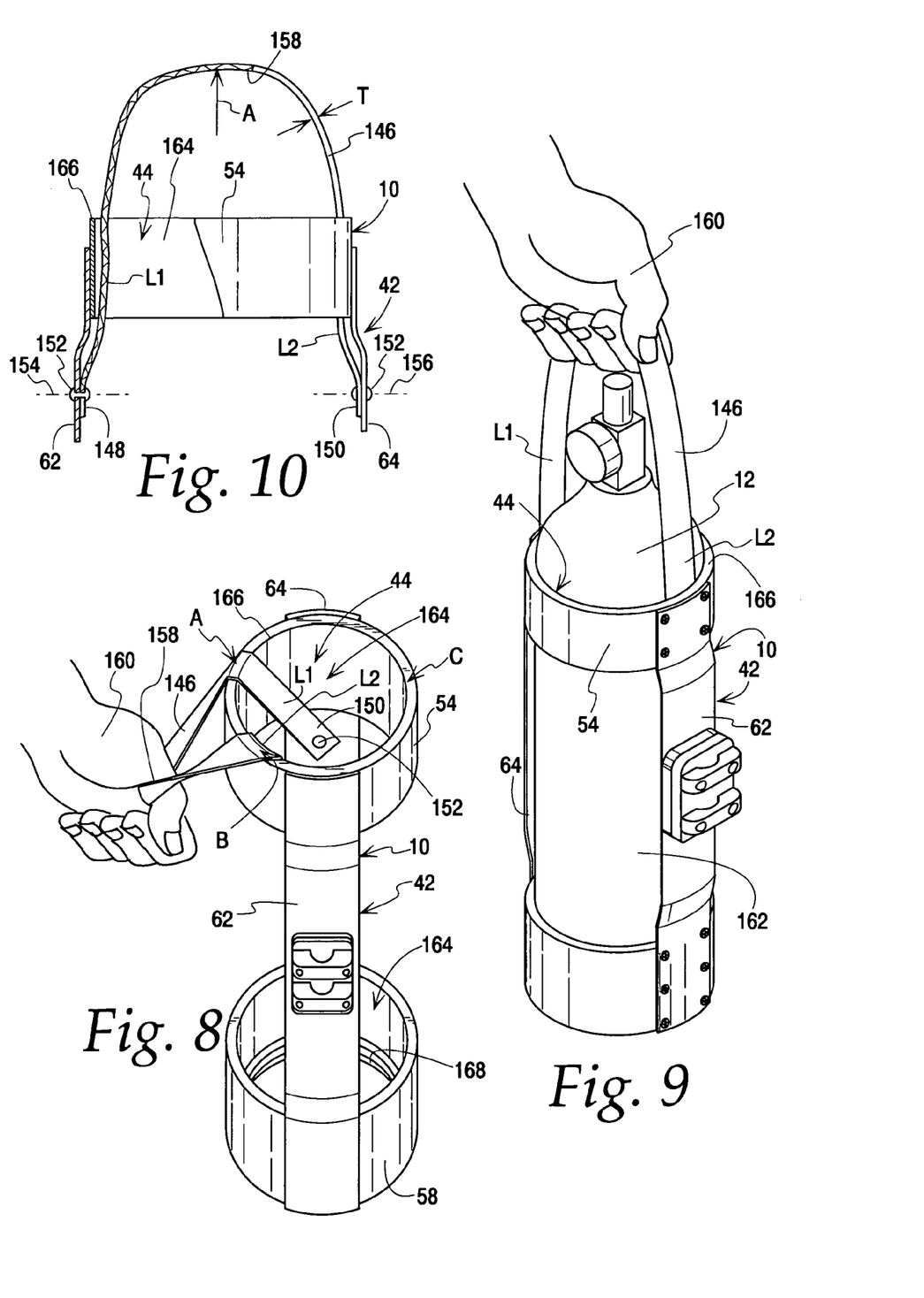
FIG. 8 is an enlarged, perspective view of the support for a cylindrically-shaped accessory, according to the invention and as shown in FIGS. 3 and 4, and including a lifting strap.
FIG. 9 is an enlarged, perspective view of the support in FIG. 8 and with a cylindrically-shaped accessory in an upright, stored orientation upon the support.
FIG. 10 is an enlarged, fragmentary, elevation view of the support in FIGS. 8 and 9 with a portion thereof broken away to reveal the connection between an end of the lifting strap and the frame on the support.

As shown in FIGS. 8-10, a lifting strap 146 may be connected to the frame 42. The lifting strap 146 potentially performs two different functions, that being: a) to provide a convenient mechanism by which the support 10 alone, or support 10 having the cylindrically-shaped accessory 12 in the upright stored orientation within the receptacle 44 defined thereby, can be maneuvered; and b) to stabilize the cylindrically-shaped accessory 12 in the upright, stored orientation.

The lifting strap 146 is made from a flexible material as commonly used for lifting components on different devices, such as luggage, etc. The lifting strap 146 has first and second ends 148, 150, respectively connected to the vertically extending reinforcing straps 62, 64 through rivets 152 or other known fasteners, such as screws, bolts, etc. The connection may be fixed or, more preferably, one that allows pivoting movement of the ends 148, 150 about horizontally extending axes 154, 156, respectively, with respect to the reinforcing straps 62, 64.

The lifting strap 146 defines an inverted, U-shaped, lifting edge 158. By grasping the lifting edge 158 with one hand 160, as shown in FIGS. 9 and 10, a lifting force can be exerted upwardly, in the direction of the arrow A in FIG. 10, thereby to apply a lifting force through the ends 148, 150 upon the reinforcing straps 62, 64, respectively. The thickness T of the lifting strap 146 may be selected so that a slight wedging action is produced between the external surface 162 of the cylindrically-shaped accessory 12 and the curved surface 164 on the frame 42 and bounding the receptacle 44 with the cylindrically-shaped accessory 12 in the upright stored orientation. This wedging occurs with the "U" defined by the lifting strap 146 vertically situated as in FIG. 9. This avoids, to a certain extent, inadvertent shifting of the cylindrically-shaped accessory 12 relative to the support 10 or rattling due to repetitive contact between the cylindrically-shaped accessory 12 and the support 10.

An additional wedging action can be produced by strategically situating the lifting strap 146 preparatory to introducing the cylindrically-shaped accessory 12 to the receptacle 44. To accomplish this, a force is exerted on the lifting strap tending to pivot the lifting strap ends 148, 150 about their respective axes 154, 156. This action is demonstrated in FIG. 8. More particularly, with the lifting strap 146 drawn taut as in FIG. 8 and drawn to a narrower "V" shape, as by the exertion of a force through one of the user's digits, the legs L1, L2 of the U-shaped lifting strap 146 bridge between their ends 148, 150 and the upper rim 166 of the upper ring 54 at locations circumferentially spaced from the reinforcing straps 62, 64. As seen most clearly in FIG. 8, the leg L1 in this state, in the absence of the cylindrically-shaped accessory 12, extends through the receptacle 44 and is loaded in tension. By directing the cylindrically-shaped accessory 12 into the support, stored orientation with the lifting strap 146 drawn taut as in FIG. 8, the lifting strap 146 is placed under additional tension. The residual forces in the lifting strap 146 cause a wedging action between each of the legs L1, L2 and the cylindrically-shaped accessory 12 at locations A and B in FIG. 8, which thereby causes the cylindrically-shaped accessory 12 to be pressed against the inside, curved surface 164 at the location C that is generally diametrically opposite to the locations A and B. Through this arrangement, pressure is applied to the cylindrically-shaped accessory 12 at three triangularly arranged locations A, B, C. The lifting strap 146 will generally remain wedged in this position once the force of the user's hand 160 is released therefrom. Thus, the lifting strap 146 tends to securely "lock" the cylindrically-shaped accessory 12 in the receptacle 44 and prevents shifting or rattling thereof.

Aside from the wedging function it provides, the lifting strap 146 also facilitates convenient lifting and transportation of the support 10 alone, or of the support 10 in combination with the cylindrically-shaped accessory 12. By exerting a substantial lifting force on the lifting strap 146 that tends to skew it from the FIG. 9 orientation, the lifting strap 146 can also be loaded in tension, whereby the cylindrically-shaped accessory 12 can be wedged in place so that it does not shift or cause rattling by shifting and acting against the frame 16 during transportation thereof.

The user can achieve this same state by manipulating the legs L1, L2 individually, as by exerting tensioning forces thereon while bracing the hand/fingers against the cylindrically-shaped accessory 12 during the process.

The connection of the lifting strap 146 may be such that it can be readily replaced with a like lifting strap 146 or one with a different material, length, flexibility, etc., as desired by the user.

The lifting strap 146 can be manually repositioned in other manners to diminish or release or increase the wedging forces, with the former facilitating separation of the cylindrically-shaped accessory 12 from the support 10.

By reason of the fact that there is an opening 168 in the lower ring 58, it is also possible for a user to extend his/her fingers through the opening 168 to press upon the cylindrically-shaped accessory 12, to facilitate vertical movement thereof out of the wedged state.

Figure 11:
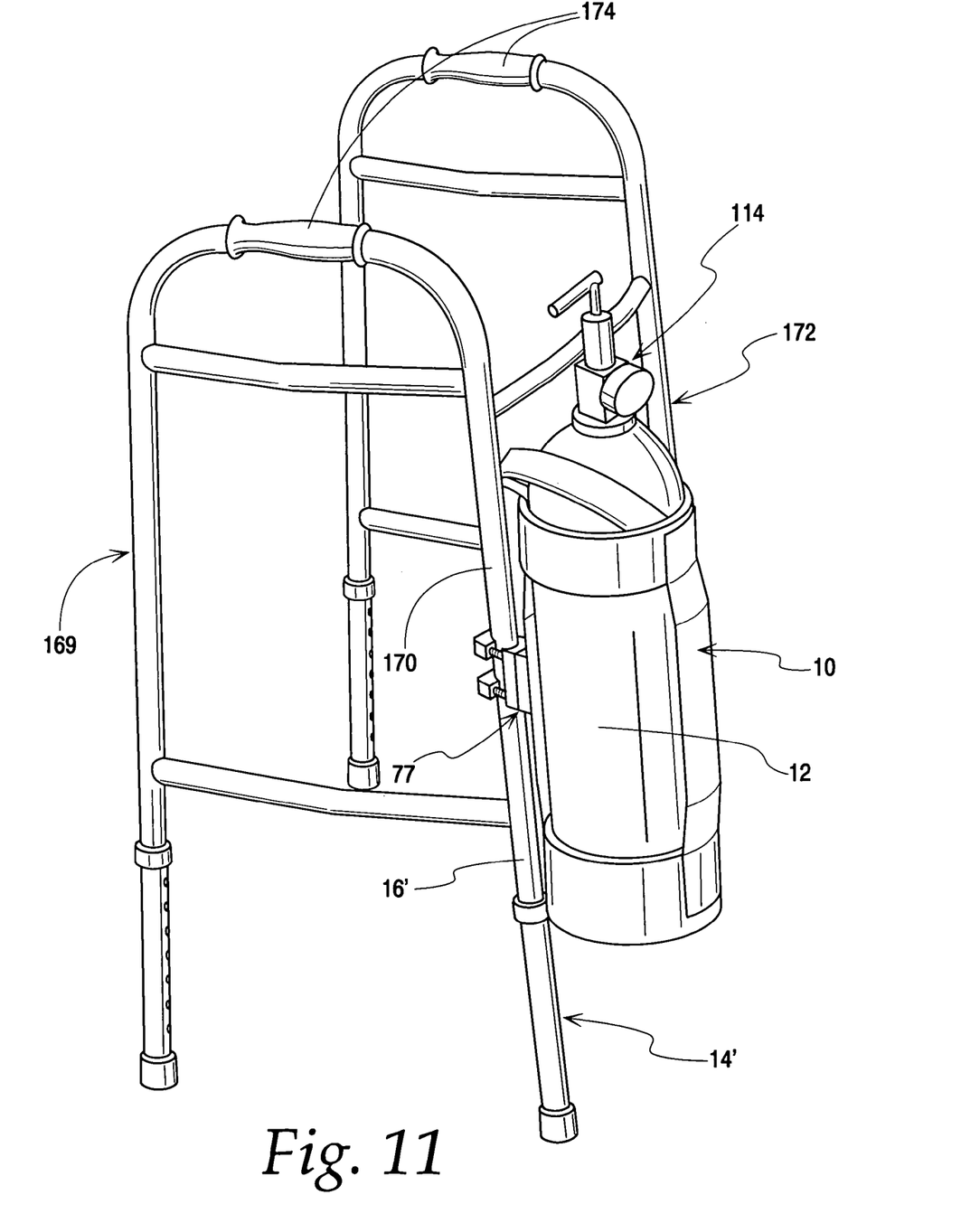
FIG. 11 is a perspective view of a walker with the support, as in FIGS. 8-10, maintained in an operative state thereon through a connecting assembly, as shown in FIGS. 4-6.

As noted above, the support 10 can be mounted to a frame on virtually an unlimited number of different devices or structures, other than the wheelchair 16, as described above. For example, as shown in FIG. 11, a frame 14' is shown on a walker 169. The walker 169 has a tubular frame 14' to which the support 10 can be operatively mounted through the connecting assembly 77. Through the connecting assembly 77, the support 10 can be operatively mounted at any location on the frame 14' that will accommodate the connecting assembly 77 and allow situation of the support 10 in a position that does not interfere with balance or operation of the walker 169. As shown in FIG. 11, the support 10 is mounted upon a vertical tubular element 170 at the front 172 of the walker 169. Through this arrangement, with the user situated to grasp the handles 174, one in each hand, the control assembly 114 is immediately and conveniently accessible. The user can conveniently reposition the cylindrically-shaped accessory 12 relative to the support 10, mounted as shown, to place/replace or remove the same.

Figure 12:
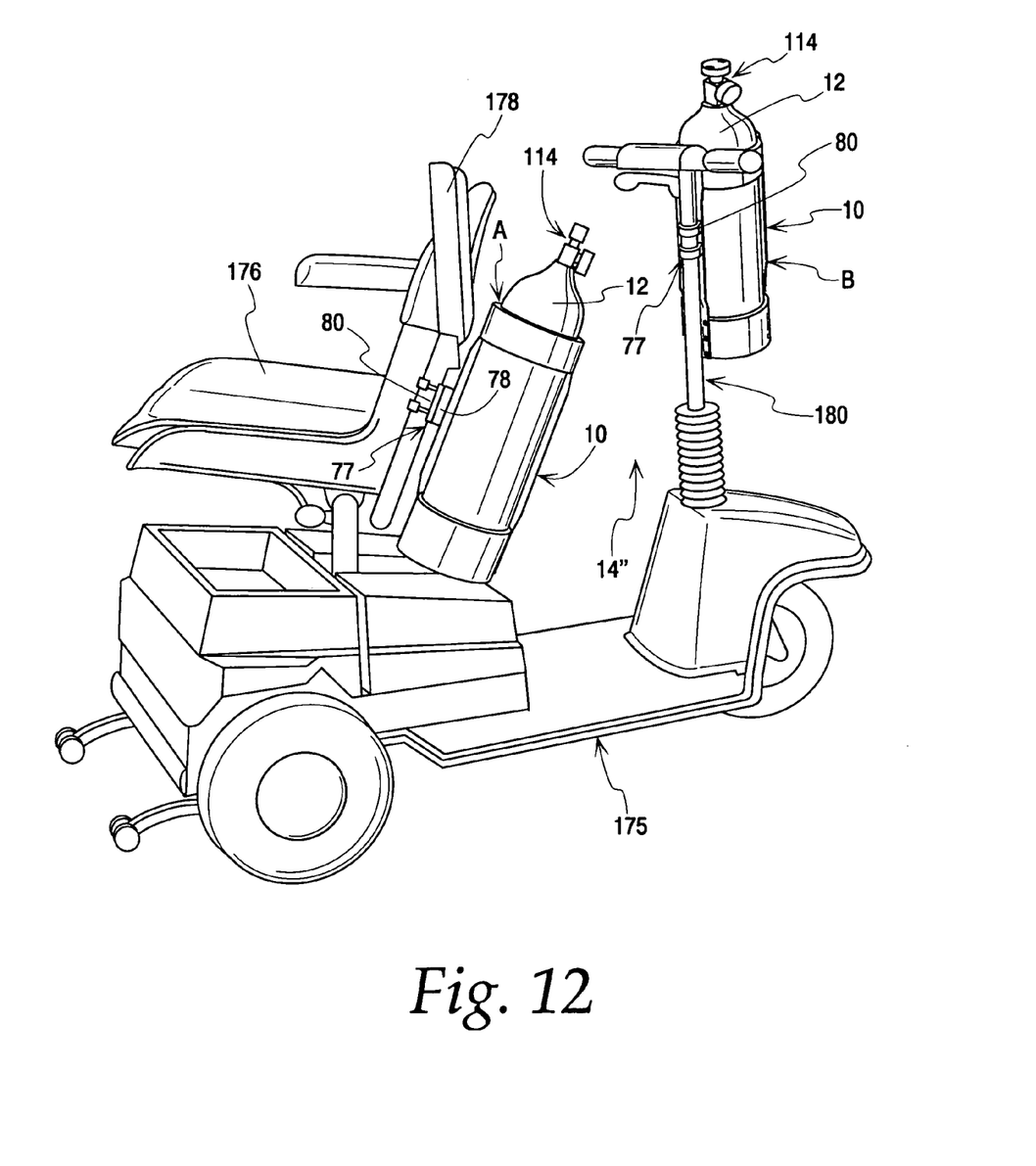
FIG. 12 is a perspective view of a scooter with the support, as in FIGS. 8-10, maintained in an operative state through the connecting assembly.

In FIG. 12, the support 10 is mounted on a frame 14" that is part of a powered scooter 175. Again, through the connecting assembly 77, the support 10 could be operatively mounted at any location, preferably where there is a tubular element that can be captively engaged by the connector parts 78, 80.

In FIG. 12, two optional mounting locations are shown, each of which facilitates seated access to the cylindrically-shaped accessory 12 in the upright stored orientation, as for placement/replacement or removal, and to the control assembly 114 thereon.

For example, the support 10 is shown mounted at location A, which is on a pivoting seat assembly 176. The cylindrically-shaped accessory 12 is thus readily accessible to a user in the seated orientation on the seat assembly 176. An arm rest 178 can be repositioned to facilitate even better access to the cylindrically-shaped container 12 from the seated orientation.

At location B, the support 10 and cylindrically-shaped accessory 12 are operatively positioned on a steering column 180. Again, with the user in the seated orientation, the cylindrically-shaped accessory 12, and the control assembly 114 thereon, are readily accessible.

Figure 13:
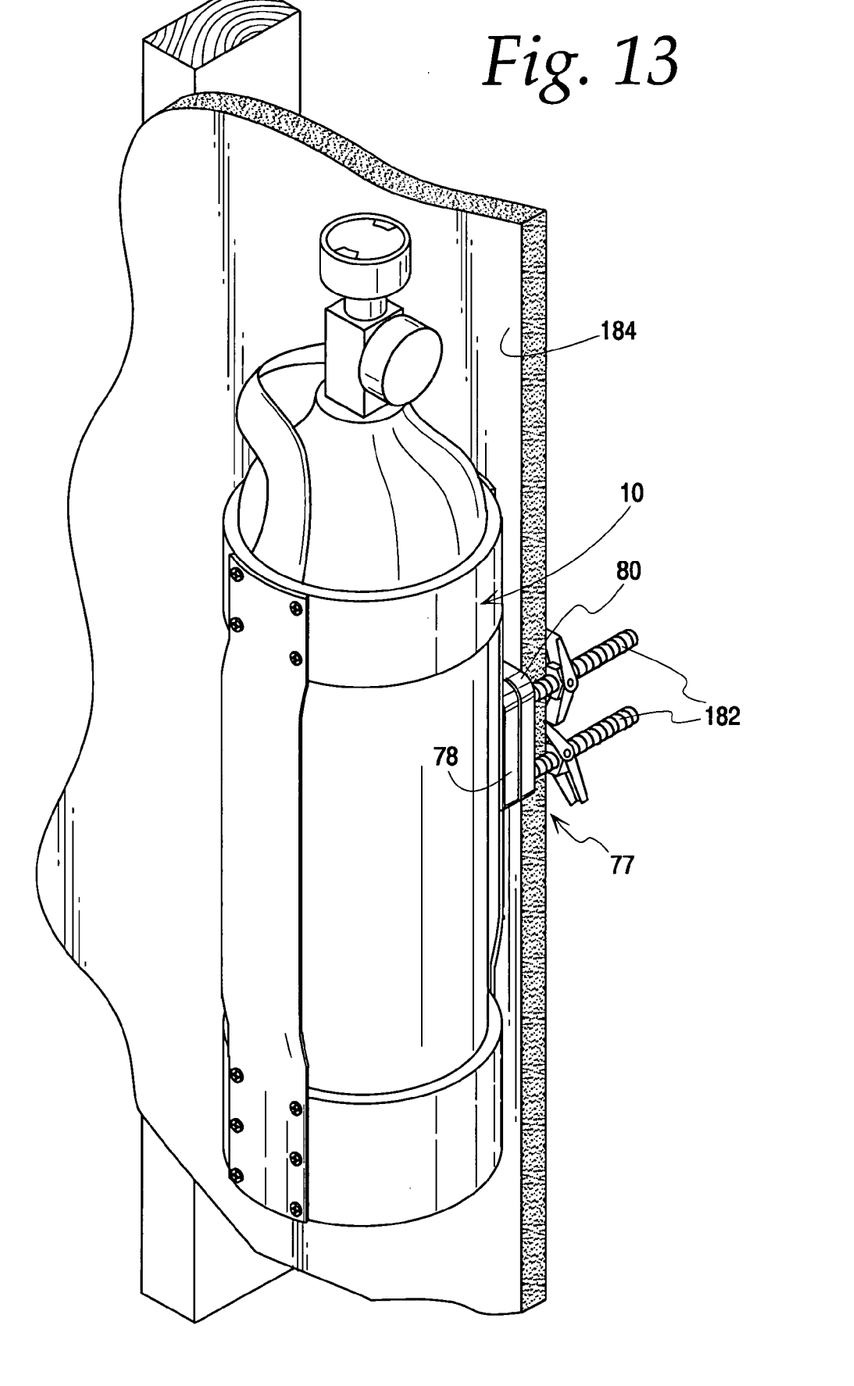
FIG. 13 is a fragmentary, perspective view of a fixed vertical wall upon which the support of FIGS. 8-10 is maintained in an operative state through the connecting assembly.

It should be understood that the connecting assembly 77 is not limited to attachment to tubular elements. As shown in FIG. 13, the connecting part 80 of the connecting assembly 77 can be connected through appropriate fasteners 182 to a fixed vertical wall 184. The connector part 78 on the support 10 can then be joined therewith to place the support 10 in the operative position shown in that Figure.

In short, the invention contemplates mounting to any frame surface or component that will accommodate the connecting assembly 77. The invention further contemplates that the support 10 might be utilized without taking advantage of the connecting assembly 77 and has the advantages associated therewith as set forth above.

The foregoing disclosure of specific embodiments is intended to be illustrative of the broad concepts comprehended by the invention.

The invention claimed is:

1. In combination:
   a cylindrically-shaped accessory; and
   a support for the cylindrically-shaped accessory, the support comprising:
   a) a first frame defining a receptacle for the cylindrically-shaped accessory, the first frame comprising:
      i) a bottom wall defining an upwardly facing surface against which the cylindrically-shaped accessory is placed in an upright stored orientation wherein a central axis of the cylindrically-shaped accessory in the upright stored orientation extends generally vertically;
      ii) a peripheral bracing wall structure,
      the peripheral bracing wall structure extending at least partially around a region occupied by the cylindrically-shaped accessory in the upright stored orientation to thereby limit tipping of the cylindrically-shaped accessory from the upright stored orientation; and
   b) a connecting assembly comprising first and second connector parts,
   the first connector part on the first frame,
   the second connector part attachable to a second frame upon which the support can be placed in an operative state,
   the first and second connector parts engagable, each with the other, by relatively translating the first and second connector parts along a connecting line between a separated position and an engaged position wherein the support is in the operative state,
   the first and second connector parts in the engaged position preventing relative movement between the first and second connector parts in directions other than along the connecting line,
   wherein the receptacle is bounded by a curved surface and the support further comprises a lifting strap that is attached to the first frame to reside between the curved surface and the cylindrically-shaped accessory in the upright stored orientation,
   wherein the lifting strap is: a) defined by a flexible material that is wedged between the cylindrically-shaped accessory and curved surface bounding the receptacle; and b) placed under tension so that residual forces within the flexible material produced by placing the flexible material under tension act against the cylindrically-shaped accessory to thereby urge the cylindrically-shaped accessory against the first frame with the cylindrically-shaped accessory in the upright stored orientation.

2. The combination according to claim 1 further in combination with a second frame to which the second connector part is attached, the second frame defined on one of: a) a wheeled device capable of seating and transporting a user; b) a walker; and c) a fixed wall.

3. The combination according to claim 1 further in combination with a second frame to which the second connector part is attached, the second frame defined on a wheeled device capable of seating and transporting a user in a seated orientation, the second connector part situated so that with the support in the operative state a user in a seated orientation on the wheeled device can access the cylindrically-shaped accessory to at least one of: a) operate the control assembly with the cylindrically-shaped accessory in the upright stored orientation; and b) change the cylindrically-shaped accessory between a separated position and the upright stored orientation.

4. The combination according to claim 1 wherein the peripheral bracing wall structure comprises a first ring extending around the receptacle with a first vertically extending axis and a vertically extending first reinforcing strap that maintains the first ring in an elevated position above the upwardly facing surface.

5. The combination according to claim 4 wherein the peripheral bracing wall structure comprises a second ring extending around the receptacle with a second vertically extending axis that is substantially coincident with the first vertically extending axis, the first reinforcing strap connecting between the first and second rings.

6. The combination according to claim 5 wherein the peripheral bracing wall structure comprises a vertically extending second reinforcing strap that connects between the first and second rings.

7. The combination according to claim 6 wherein the first and second reinforcing straps are generally diametrically oppositely located with respect to each other.

8. The support for a cylindrically-shaped accessory according to claim 5 wherein the peripheral bracing wall structure comprises a third ring extending around the receptacle with a vertically extending third axis, the first reinforcing strap connecting between the first, second and third rings.

9. The combination according to claim 1 wherein the peripheral bracing wall structure comprises first and second vertically spaced rings extending around the receptacle and the bottom wall is on one of the first and second rings.

10. The combination according to claim 9 wherein the one of the first and second rings has a top and bottom and the upwardly facing surface resides between the top and bottom of the one of the first and second rings.

11. The combination according to claim 10 wherein the one of the first and second rings has a continuous wall that extends around the receptacle and the bottom wall is formed as one piece with the continuous wall.

12. The combination according to claim 4 wherein the first ring comprises plastic and the first reinforcing strap comprises metal.

13. The combination according to claim 4 wherein the first ring has a curved surface and the first strap is substantially flat and locally shaped to conform to the curved surface.

14. The combination according to claim 1 wherein the receptacle is bounded by a curved surface and further comprising a lifting strap that is attached to the first frame to reside between the curved surface and a cylindrically-shaped accessory in the upright stored orientation.

15. The combination according to claim 14 wherein the lifting strap has a downwardly opening U-shaped surface upon which a lifting force can be applied by a user to elevate the support together with the cylindrically-shaped accessory in the upright stored orientation.

16. The combination according to claim 15 wherein the lifting strap is defined by a flexible material that becomes wedged between the cylindrically-shaped container and curved surface bounding the receptacle by applying a tensioning force to the lifting strap.

17. The combination according to claim 15 wherein the receptacle is cylindrically shaped with a vertical central axis and the lifting strap has spaced first and second legs that are attached one each to the first frame at first and second locations spaced circumferentially around the vertical central axis of the receptacle.

18. The combination according to claim 17 wherein the first and second legs are attached to the first frame for pivoting movement relative to the frame respectively around first and second axes.

19. In combination:
a) a cylindrically-shaped accessory containing a pressurized supply of gas and having a control assembly; and
b) a support for the cylindrically-shaped accessory, the support comprising a first frame comprising:
a first ring having a first central axis;
a second ring having a second central axis;
first and second reinforcing straps extending between the first and second rings,
the first and second reinforcing straps: i) maintaining the first and second rings in coaxial and axially spaced relationship; and ii) circumferentially spaced from each other with respect to the central axes;
a bottom wall defining an upwardly facing surface,
the first and second rings and upwardly facing surface bounding a receptacle into which the cylindrically-shaped container can be directed into an upright stored orientation in which the cylindrically-shaped container bears on the upwardly facing surface and is surrounded by the first and second rings,
the cylindrically-shaped container translatable relative to the support selectively: i) axially downwardly from a separated position into the upright stored orientation within the receptacle; and ii) axially upwardly from the upright stored orientation to be separated from the support; and
a second frame to which the second connector part is attached, the second frame defined on a wheeled device capable of seating and transporting a user in a seated orientation, the second connector part situated so that with the support in the operative state a user in a seated orientation on the wheeled device can access the cylindrically-shaped accessory to at least one of: a) operate the control assembly with the cylindrically-shaped accessory in the upright stored orientation; and b) change the cylindrically-shaped accessory between a separated position and the upright stored orientation.

20. The combination according to claim 19 wherein the first ring has a curved surface and the first reinforcing strap is substantially flat and locally shaped to conform to the curved surface.

21. The combination according to claim 19 wherein a lifting strap is provided on the first frame and defines an inverted U-shaped surface upon which a lifting force can be applied, the lifting strap configured so that application of a tensioning force on the lifting strap causes the lifting strap to wedge a cylindrically-shaped accessory in the upright stored orientation against the first frame.

22. In combination:
a) a cylindrically-shaped accessory; and
b) a support for the cylindrically-shaped accessory, the support comprising:
a first frame defining a receptacle for the cylindrically-shaped accessory, the first frame comprising:
i) a bottom wall defining an upwardly facing surface against which the cylindrically-shaped accessory can be placed in an upright stored orientation wherein a central axis of the cylindrically-shaped accessory in the upright stored orientation extends generally vertically;

ii) a peripheral bracing wall structure;

a lifting strap;

the peripheral bracing wall structure extending at least partially around a region occupied by the cylindrically-shaped accessory in the upright stored orientation to thereby limit tipping of a cylindrically-shaped accessory from the upright stored orientation; and a second frame;

the first frame attached to the second frame upon which the support can be placed in an operative state, wherein the lifting strap defines an inverted U-shaped surface upon which a lifting force can be applied, the lifting strap configured so that application of a tensioning lifting force on the lifting strap causes residual tensioning forces in the lifting strap produced by the lifting force to urge the cylindrically-shaped accessory against the first frame with the lifting force applied and thereafter released.

23. The combination according to claim 22 wherein the second frame is defined on one of: a) a wheeled device capable of seating and transporting a user; b) a walker; and c) a fixed wall.

24. A support for a cylindrically-shaped accessory, the support comprising a first frame comprising:

a first ring having a first central axis;

a second ring having a second central axis;

first and second reinforcing straps extending between the first and second rings, the first and second reinforcing straps: i) maintaining the first and second rings in coaxial and axially spaced relationship; and ii) circumferentially spaced from each other with respect to the central axes; and a bottom wall defining an upwardly facing surface, the first and second rings and upwardly facing surface bounding a receptacle into which a cylindrically-shaped container can be directed into an upright stored orientation in which the cylindrically-shaped container bears on the upwardly facing surface and is surrounded by the first and second rings, a cylindrically-shaped container translatable relative to the support selectively: i) axially downwardly from a separated position into the upright stored orientation within the receptacle; and ii) axially upwardly from the upright stored orientation to be separated from the support, wherein a lifting strap is provided on the first frame and defines an inverted U-shaped surface upon which a lifting force can be applied, the lifting strap configured so that application of a tensioning force on the lifting strap causes residual tensioning forces in the lifting strap to cause the lifting strap to wedge a cylindrically-shaped accessory in the upright stored orientation against the first frame both: a) with the lifting force applied; and b) thereafter with the lifting force released.

* * * * *